United States Patent [19]

Walsh

[11] 4,254,146
[45] Mar. 3, 1981

[54] 3-BENZOYL-2-NITROPHENYLACETIC ACIDS, METAL SALTS, AMIDES AND ESTERS

[75] Inventor: David A. Walsh, Richmond, Va.

[73] Assignee: A. H. Robins Company, Inc., Richmond, Va.

[21] Appl. No.: 86,195

[22] Filed: Oct. 18, 1979

[51] Int. Cl.³ .................. A61K 31/24; C07C 79/46
[52] U.S. Cl. ............................... 424/309; 564/166; 424/319; 424/324; 560/21; 562/436
[58] Field of Search ............ 562/436; 260/559 D, 260/559 P, 558 R; 560/21; 424/309, 319, 324

[56] References Cited

U.S. PATENT DOCUMENTS

| | | | |
|---|---|---|---|
| 3,828,093 | 8/1974 | Bays et al. | 562/436 |
| 4,045,576 | 8/1977 | Welstead, Jr. et al. | 562/436 |
| 4,126,635 | 11/1978 | Welstead, Jr. et al. | 562/436 |

OTHER PUBLICATIONS

Beilstein: Organic Chemistry 10, 361 (1910–1919).
Zinic et al., Chem. Absts., 88, 105282(p), 1978.

Primary Examiner—Natalie Trousof
Assistant Examiner—G. T. Breitenstein

[57] ABSTRACT

3-Benzoyl-2-nitrophenylacetic acids, metal salts, amides and esters are disclosed having the formula:

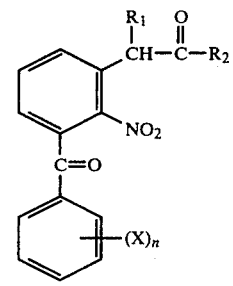

wherein $R_1$ is hydrogen or lower alkyl; $R_2$ is OH, OM, O-lower alkyl, $NH_2$, NH-lower alkyl or N,N-dilower alkyl; X is hydrogen, halogen, lower alkyl, lower alkoxy, trifluoromethyl or nitro and M is a pharmaceutically acceptable cation or a fraction thereof when the cation is multivalent, hydrates thereof and n is 1–3 inclusive. The compounds have anti-inflammatory activity and methods and pharmaceutical compositions for use thereof are disclosed.

18 Claims, No Drawings

3-BENZOYL-2-NITROPHENYLACETIC ACIDS, METAL SALTS, AMIDES AND ESTERS

BACKGROUND OF THE INVENTION

1. Field of the Invention

The present invention is concerned with certain novel 3-benzoyl-2-nitrophenylacetic acids and derivatives; metal acid salts, amides, and esters, pharmaceutical methods of treatment, pharmaceutical compositions and use thereof and methods of producing the same and novel intermediates. The 3-benzoyl-2-nitrophenylacetic acids and derivatives are anti-inflammatory agents having minimal side effects on internal administration to living animal bodies.

2. Description of the Prior Art

2-Amino-3-benzoylphenylacetic acids, esters and metal salts thereof having anti-inflammatory activity are disclosed in U.S. Pat. No. 4,045,576.

An isomer, 4-benzoyl-2-nitrophenylacetic acid was reported in Beilstein: Organic Chemistry 10, 361 (1910-1919).

Another isomer, 3-benzoyl-4-nitrophenyl-2-propionic acid was reported by Fenic et al., J. Het. Chem. 14, 1225 (1977) as an intermediate in the preparation of benzodiazepines.

Generally, in the past, strong anti-inflammatory drugs have been found to produce serious side effects of gastric bleeding and ulceration when administered orally to animals in the effective range. The compounds of the present invention have been found to have the advantage that low incidence of gastric irritation is observed when they are administered in the effective range for reducing inflammation as compared to indomethacin and the 2-amino-3-benzoylphenylacetic acids disclosed in U.S. Pat. No. 4,045,576.

SUMMARY OF THE INVENTION AND OBJECTS

The novel compounds exhibiting anti-inflammatory activity of the present invention are 3-benzoyl-2-nitrophenylacetic acids, metal acid salts, amides and esters illustrated generally by the following formula:

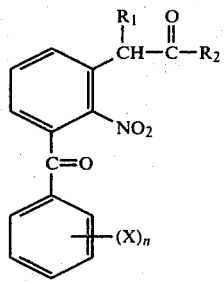

Formula I wherein;

$R_1$ is hydrogen or lower alkyl, $R_2$ is OH, OM, O-lower alkyl, $NH_2$, NH-lower alkyl, or —N,N-dilower alkyl, X is hydrogen, halogen, lower alkyl, lower alkoxy, trifluoromethyl or nitro, M is a pharmaceutically acceptable cation or a fraction thereof when the cation is multivalent, hydrates thereof and n is 1-3 inclusive.

Other novel compounds of the present invention which are 2-(3-benzoyl-2-nitrophenyl)alkanedioic acid dialkyl ester intermediates in the preparation of the anti-inflammatory compounds of this invention have the formula:

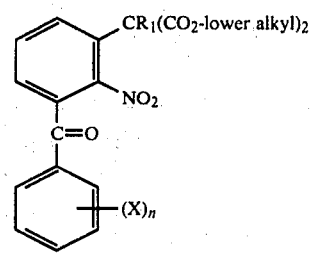

Formula II wherein $R_1$, X and n are as defined hereinabove. Compounds of Formula II wherein lower alkyl is ethyl are preferred.

In the definitions of symbols in the formulas hereof and where they appear elsewhere throughout this specification, the terms have the following significance.

The term "lower alkyl" as used herein includes straight and branched chain radicals of up to eight carbon atoms and is exemplified by such groups as methyl, ethyl, propyl, isopropyl, butyl, sec. butyl, tertiary butyl, amyl, isoamyl, hexyl, heptyl and octyl. The term "lower alkoxy" has the formula —O-lower alkyl.

The term "halogen" when referred to herein includes fluorine, chlorine and bromine and iodine, preferably fluorine, chlorine and bromine.

The term "pharmaceutically acceptable cation" forming salts of the acids and hydrates thereof when referred to herein includes any pharmaceutically acceptable metal cation as exemplified by sodium, potassium, calcium, magnesium, zinc, copper and aluminum and water of hydration. Sodium cation is preferred.

Anti-inflammatory activity was demonstrated in laboratory animals using (1) a modification of the Evans-Blue Carrageenan Pleural Effusion Assay of Sancilio, L. F., J. Pharmacol. Exp. Ther. 168, 199-204 (1969), (2) The Method of Walz et al., J. Pharmacol. Exp. Ther. 178, 223-231 for Adjuvant-Induced Arthritis in Rats, and (3) Carrageenan-Induced Foot Edema Method of Winter et al., Proc. Soc. Exp. Biol. Med. 111: 544-547 (1962).

When tested in comparison with indomethacin in the Pleural Effusion Assay referred to above, the compounds of the present invention are generally slightly less potent than indomethacin but exhibit only a small fraction of the gastric irritation found with indomethacin.

The isomer referred to hereinabove, 4-benzoyl-2-nitrophenylacetic acid, was prepared and tested and found to have no anti-inflammatory activity at 100 mg/kg in the Evans-Blue Carrageenan Pleural Effusion Assay compared to strong activity of the compound of Example 4 at 4 mg/kg.

It is, therefore, an object of the present invention to provide novel 3-benzoyl-2-nitrophenylacetic acids, acid salts and hydrates, amides and esters thereof.

Another object is to provide a novel method for the treatment of a living animal body and especially a mammalian body for the purpose of alleviating inflammation with a minimum of undesirable side effects in the gastric and intestinal area utilizing 3-benzoyl-2-nitrophenylacetic acids, amides and esters thereof and therapeutic compositions therefor.

It is also an object of the present invention to provide novel intermediates.

Additional objects will become apparent to one skilled in the art and still others will become apparent hereinafter.

DETAILED DESCRIPTION OF THE INVENTION AND PREFERRED EMBODIMENTS

The intermediates of Formula II are prepared according to the following equations:

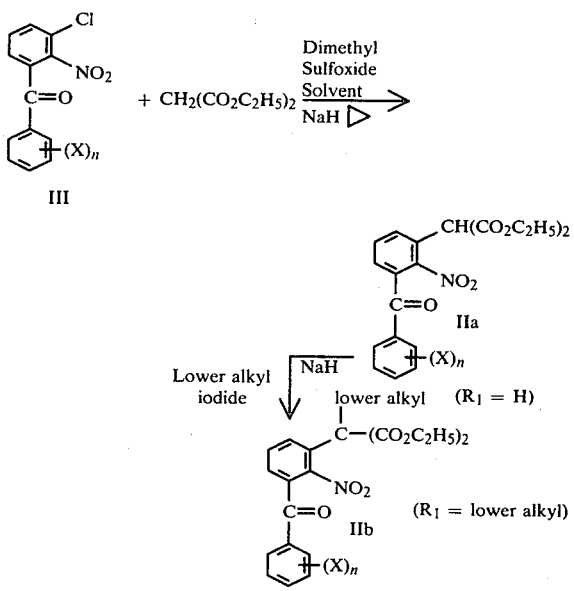

wherein X and n are as defined hereinabove. Formulas IIa and IIb are encompassed by Formula II.

The 3-benzoyl-2-nitrophenylacetic acids and metal salts of Formula I wherein $R_2$ is OH and OM are prepared according to the following equations:

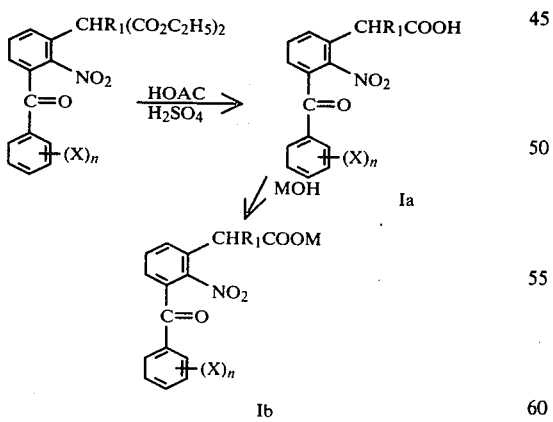

$R_1$, X, n and M are as defined hereinabove.

The 3-benzoyl-2-nitrophenylacetic acids are converted to amides ($R_2$=NH$_2$), lower alkyl amides ($R_2$=NH lower alkyl), di-lower alkyl amides [($R_2$=N-(lower alkyl)$_2$] and esters (R=O-lower alkyl) by reactions represented by the following equations:

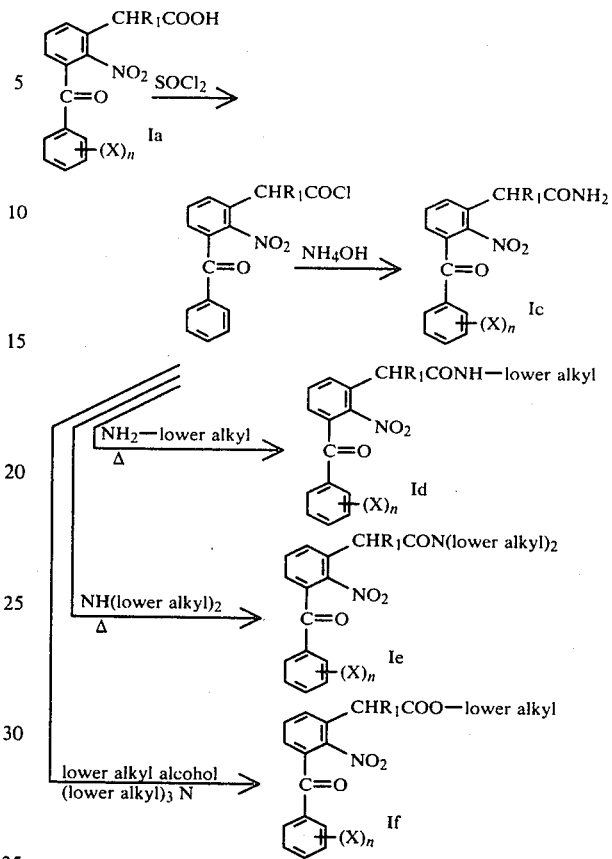

$R_1$, X and n are as defined hereinabove. Formulas Ia through If are encompassed by Formula I.

The starting materials III for preparing the 3-benzoyl-2-nitrophenylacetic acids are prepared as represented by the following equation:

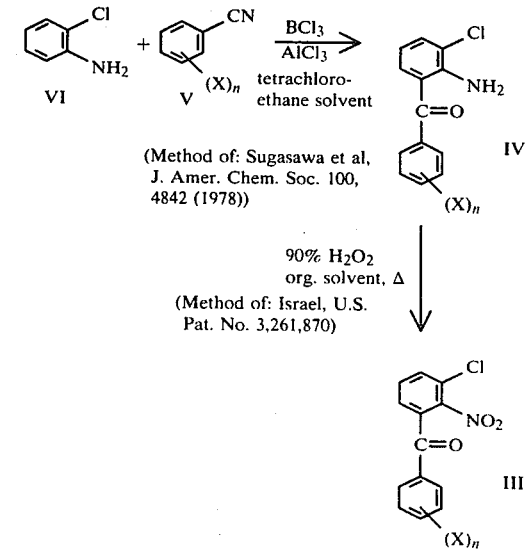

X and n are as defined hereinabove. The procedure for preparing the starting materials III and IV is illustrated more fully in Preparations 1 to 6.

PREPARATION 1

[2-Amino-3-chlorophenyl]phenylmethanone

To a cold solution of 36.1 g (0.30 mole) of 2-chloroaniline in 200 ml of 1,1,2,2-tetrachloroethane was added successively a cold solution of 34.0 g (0.33 mole) of boron trichloride in 150 ml of tetrachloroethane, 60 ml (0.6 mole) of benzonitrile and 44.0 g (0.33 mole) of aluminum trichloride. The solution was heated at reflux for 5 hr, cooled and treated with 200 ml of 2N HCl and then heated on a steam bath for 0.5 hr. The layers were separated and the organic layer was dried over sodium sulfate and concentrated. The residue was subjected to vacuum distillation at 100° and 0.2 mm Hg pressure. The pot residue was chromatographed on 250 g silica gel to yield 43.6 (63%) of yellow powder which melted at 54°-56° C. after recrystallizing from ligroin.

Analysis: Calculated for $C_{13}H_{10}ClNO$: C,67.40; H,4.35; N,6.05. Found: C,67.41; H,4.35; N,6.06.

PREPARATION 2

[2-Amino-3-chlorophenyl][4-chlorphenyl]methanone

To a cold solution of 44.4 g (0.35 mol) of 2-chloroaniline in 100 ml of 1,1,2,2-tetrachloroethane was added a solution of 44.6 g (0.38 mol) of boron trichloride in 100 ml of tetrachloroethane, followed by a solution of 100 g (0.73 mol) of 4-chlorobenzonitrile in 225 ml tetrachloroethane and 50.5 g (0.38 mol) of aluminum trichloride. The solution was heated at reflux for 5 hrs, cooled, treated with 240 ml of 2N hydrochloric acid and heated on a steam bath for 0.5 hr. The mixture was cooled and filtered through celite. The filtrate layers were separated and the organic layer was concentrated. The residue was subjected to vacuum distillation at 100° and 0.2 mm. The pot residue (105 g) was chromatographed on 400 g silica gel to give 58.4 g of an oil which crystallized. The solid was recrystallized twice from i-PrOH to yield 33.0 g (35%) of yellow needles, m.p. 85° C.

Analysis: Calculated for $C_{13}H_9ClNO$: C,58.67; H,3.41; N,5.26. Found: C,58.73; H,3.38; N,5.31.

PREPARATION 3

[3-Chloro-2-nitrophenyl]phenylmethanone.

To a cold, stirred mixture of 10.8 ml of 90% hydrogen peroxide and 250 ml of methylene chloride was added 100 g (67.6 ml) of trifluoroacetic anhydride dropwise over a 45-min period. The ice bath was removed and a solution of 23.1 g (0.1 mol) of crude [2-amino-3-chlorophenyl]phenylmethanone in 100 ml methylene chloride was added dropwise over a 45-min period. The dark solution was heated on a steambath for 1 hr, cooled, and washed successively with two 200-ml portions of cold water, two 200-ml portions of cold 10% sodium carbonate (emulsion) and once with saturated sodium chloride solution. The methylene chloride solution was dried over sodium sulfate and concentrated to give 19.6 g of an oil as residue. The oil was chromatographed on 250 g of silica gel to give 15.3 g (59%) of an oil which crystallized upon scratching. This solid was recrystallized from isopropanol to yield a tan solid, m.p. 67°-69° C.

Analysis: Calculated for $C_{13}H_8ClNO_3$: C,59.67; H,3.08; N,5.35. Found: C,59.78; H,3.06; N,5.35.

PREPARATION 4

[3-Chloro-2-nitrophenyl][4-chlorophenyl]methanone

To a cold, stirred mixture of 10.0 ml of 90% hydrogen peroxide and 250 ml of methylene chloride was added dropwise 100 g of trifluoroacetic anhydride over a 1-hr period. The ice bath was removed and a solution of 26.6 g (0.10 mol) of [2-amino-3-chlorophenyl][4-chlorophenyl]methanone in 100 ml methylene chloride was added dropwise over a 1-hr period. The dark solution was then heated on a steambath for 1 hr, cooled, and washed successively with two 200-ml portions of cold water, two 200-ml portions of cold 10% sodium carbonate and once with the saturated sodium chloride solution. The methylene chloride layer was dried over sodium sulfate and concentrated to give 19.9 g of tan solid as residue. The solid was chromatographed on 400 g of silica gel to yield 11.9 g (40%) of desired product. A portion was recrystallized twice from acetonitrile and once from absolute ethanol to yield an analytical sample of a white solid, m.p. 147°-148° C.

Analysis: Calculated for $C_{13}H_7ClNO_3$: C,52.73; H,2.38; N,4.73. Found: C,53.11; H,2,38; N,4.85.

PREPARATION 5

Following the procedure of Preparation 2 but substituting equal molar amounts of the following for 4-chlorobenzonitrile:

2,4-dichlorophenyl methanone,
4-methylphenyl methanone,
4-methoxyphenyl methanone,
4-nitrophenyl methanone,
there are obtained
(2-amino-3-chlorophenyl)(2,4-dichlorophenyl)methanone,
(2-amino-3-chlorophenyl)(4-methylphenyl)methanone,
(2-amino-3-chlorophenyl)(4-methoxyphenyl)methanone,
(2-amino-3-chlorophenyl)(4-nitrophenyl)methanone.

PREPARATION 6

Following the procedure of Preparation 4 but substituting equal molar amounts of the following for (2-amino-3-chlorophenyl)(4-chlorophenyl)methanone:

(2-amino-3-chlorophenyl)(2,4-dichlorophenyl)methanone,
(2-amino-3-chlorophenyl)(4-methylphenyl)methanone,
(2-amino-3-chlorophenyl)(4-methoxyphenyl)methanone, and
(2-amino-3-chlorophenyl)(4-nitrophenyl)methanone
there are obtained
(3-chloro-2-nitrophenyl)(2,4-dichlorophenyl)methanone,
(3-chloro-2-nitrophenyl)(4-methylphenyl)methanone,
(3-chloro-2-nitrophenyl)(4-methoxyphenyl)methanone, and
(3-chloro-2-nitrophenyl)(4-nitrophenyl)methanone.

The novel compounds of the present invention and the method of preparation is exemplified more fully by the following illustrative examples. The scope of the invention is, however, not limited thereto.

EXAMPLE 1

2-(3-Benzoyl-2-nitrophenyl)propanedioic Acid, Diethyl Ester

A mixture of 1.9 g (0.044 mole) of 57% sodium hydride/oil washed with petroleum ether in 25 ml of dry dimethylsulfoxide was heated to 100° C. and treated with a solution of 7.0 g (0.044 mol) of diethylmalonate in 25 ml of dimethylsulfoxide. The mixture was stirred until all solids had dissolved and then a solution of 5.4 g (0.021 mol) of [3-chloro-2-nitrophenyl]phenylmethanone in 15 ml of dimethylsulfoxide was added. The dark solution was heated at 100° C. for 1 hr and then poured into 800 ml of ice water. The mixture was extracted with three 100-ml portions of benzene and the combined extracts were washed twice with water, once with saturated sodium chloride solution, dried over sodium sulfate and concentrated to give a solid as residue. The solid was recrystallized from isopropanol to yield 3.1 g (46%) of product, m.p. 130°–131° C.

Analysis: Calculated for $C_{20}H_{19}NO_7$: C,62.34; H,4.97; N,3.64. Found: C,62.31; H,5.03; N,3.60.

EXAMPLE 2

2-[3-(4-Chlorobenzoyl)-2-nitrophenyl]propanedioic Acid Diethyl Ester

A mixture of 3.9 g (0.080 mol of 50% sodium hydride/oil washed with petroleum ether in 50 ml of dimethylsulfoxide was heated to 100° and treated with a solution of 12.8 g (0.080 mol) of diethylmalonate in 15 ml of dimethylsulfoxide. The mixture was stirred until all solids dissolved and then a solution of 11.0 g (0.037 mol) of [3-chloro-2-nitrophenyl][4-chlorophenyl]methanone in 35 ml dimethylsulfoxide was added. The dark solution was heated at 90°–100° C. for 2 hrs and then poured into 1 liter of water and let stand overnight. A solid (5.5 g) was collected by filtration. The filtrate was extracted twice with benzene. The combined extracts were washed with water and saturated sodium chloride solution, dried over sodium sulfate and concentrated to give an oil as residue. The oil was dissolved in a small volume of isopropyl alcohol and seeded with the collected solid. An additional 3.1 g of product was obtained to yield a total solids yield of 8.6 g (55%), m.p. 96°–100° C.

Analysis: Calculated for $C_{20}H_{18}ClNO_7$: C, 57.22; H,4.32; N,3.34. Found: C,57.19; H,4.26; N,3.53.

EXAMPLE 3

2-(3-Benzoyl-2-nitrophenyl)-2-methylpropanedioic Acid Diethyl Ester

A slurry of 0.6 g (0.012 mole) of 50% sodium hydride/oil (washed, petroleum ether) in a 10 ml dimethylformamide was treated dropwise with a solution of 3.6 g (0.009 mole) of 2-(3-benzoyl-2-nitrophenyl)-propanedioic acid diethyl ester in 20 ml of dimethylformamide. The mixtue was stirred for 5 min and the 4 ml (9.1 g, 0.065 mole) of methyliodide was added and the solution stirred at ambient temperature overnight. The solution was poured into 500 ml of cold water and let stand overnight. The aqueous layer was decanted and the gummy residue was dissolved in diethylether. The ether solution was washed with water and saturated sodium chloride solution, dried over sodium sulfate and concentrated to give 3.5 g (95%) of a gray solid, m.p. 102°–104° C. (recrystallized from 2-propanol).

Analysis: Calculated for $C_{21}H_{21}NO_7$: C,63.15; H,5.30; N,3.51. Found: C,63.27; H,5.34; N,3.50.

EXAMPLE 4

3-Benzoyl-2-nitrobenzeneacetic Acid

A solution of 11.5 g (0.03 mole) of 2-(3-benzoyl-2-nitrophenyl)propanedioic acid in 50 ml of 20% sulfuric acid and 50 ml of acetic acid was heated at reflux under a nitrogen atmosphere overnight. The solution was concentrated and the residue was made basic with 450 ml of 2N potassium bicarbonate. The mixture was extracted twice with diethylether and the aqueous layer was made acidic with 20 ml of conc. sulfuric acid. The solid which precipitated was collected by filtration, washed with water, recrystallized from aqueous isopropanol to yield 4.1 g (48%) of brown solid, m.p. 160°–162° C.

Analysis; Calculated for $C_{15}H_{11}NO_5$: C,63.16; H,3.89; N,4.91. Found: C,63.15; H,3.89; N,4.90.

EXAMPLE 5

3-(4-Chlorobenzoyl)-2-nitrobenzeneacetic Acid

A solution of 6.9 g (0.017 mol) of 2-[3-(4-chlorobenzoyl)-2-nitrophenyl]propanedioic acid in 40 ml of 20% sulfuric acid and 40 ml of acetic acid was heated at reflux under a nitrogen atmosphere overnight. The reaction mixture was cooled, and the solid which precipitated was collected by filtration and stirred with 150 ml of 5% sodium bicarbonate. The mixture was filtered and the filtrate was made acidic with concentrated sulfuric acid. The resulting white solid was collected by filtration and recrystallized from aqueous isopropyl alcohol to yield 3.2 g (61%) of white needles, m.p. 164°–165° C.

Analysis: Calculated for $C_{15}H_{10}ClNO_5$: C,56.35; H,3.15; N,4.38. Found: C,56.56; H,3.10; N,4.52.

EXAMPLE 6

3-Benzoyl-2-nitro(α-methyl)benzeneacetic Acid

A mixture of 3.0 g (0.0075 mole) of 2-(3-benzoyl-2-nitrophenyl)-2-methylpropanedioic acid, 20 ml of acetic acid and 20 ml of 20% sulfuric acid was heated at reflux under a nitrogen atomsphere overnight. The dark solution was concentrated and the residue was treated with 200 ml of 2N potassium carbonate. The mixture was triturated with diethyl ether and then filtered to remove insoluble material. The filtrate layers were separated and the aqueous layer was washed with diethylether. The aqueous solution was treated with charcoal, filtered through celite and the filtrate made acidic with 13 ml of conc. sulfuric acid. The solid which precipitated was collected by filtration and recrystallized from 2-propanol-water to yield 0.4 g (18%) of white powder, m.p. 177°–179° C.

Analysis: Calculated for $C_{16}H_{13}NO_5$: C,64.21; H,4.38; N,4.61. Found: C,64.43; H,4.44; N,4.71.

EXAMPLE 7

3-Benzoyl-2-nitrophenylacetamide

A mixture of 8.1 g (0.028 mole) of 3-benzoyl-2-nitrobenzeneacetic acid, 50 ml of thionylchloride and 50 ml of benzene was heated at reflux overnight. The dark solution was concentrated and the residue was chased twice with benzene to give 8.1 g (94%) of the acid chloride as an oil. A solution of 4.0 g (0.013 mole) of the acid chloride in 20 ml of tetrahydrofuran was added to 50 ml of concentrated ammonium hydroxide with vigorous stirring. The mixture was stirred for 1 hr at room temperature and then 200 ml of cold water was added. The mixture was extracted with three 75 ml portions of diethylether. The combined diethylether extracts were washed with water, dried over sodium sulfate and concentrated to give the crude amide as a gum which crystallized upon standing overnight. The solid was recrystallized from benzene to yield 1.4 g (38%); m.p. 137°–139° C. (d).

Analysis: Calculated for $C_{15}H_{12}N_2O_4$: C,63.38; H, 4.26; N,9.85. Found: C,63.24; H,4.17; N,9.72.

EXAMPLE 8

Ethyl 3-benzoyl-2-nitrophenylacetate

The acid chloride of 3-benzoyl-2-nitrobenzeneacetic acid was prepared in the same manner as in Example 7. A solution of 2.0 g (0.006 mole) of the resulting acid chloride in 10 ml THF was treated with 50 ml of absolute ethyl alcohol and 5 ml of triethylamine. The mixture was stirred at ambient temperature for 2 hrs. concentrated, and the residue partitioned between methylene chloride and water. The methylene chloride layer was dried over sodium sulfate and concentrated to give a dark gum as residue. The residue was dissolved in diethylether and filtered to remove dark, insoluble impurities. The filtrate was concentrated to give a gum which eventually crystallized after standing for 3 weeks. The solid was recrystallized twice from isopropyl alcohol (charcoal) to yield 0.4 g (19%) of a pale, yellow powder, m.p. 83°–85° C.

Analysis: Calculated for $C_{17}H_{15}NO_5$: C,65.17; H,4.83; N,4.47. Found: C,65.05; H,4.83; N,4.46.

EXAMPLE 9

Following the procedure of Example 2 but substituting equal molar amounts of the following for (3-chloro-2-nitrophenyl)(4-chlorophenyl)methanone:
(3-chloro-2-nitrophenyl)-2,4-dichlorophenyl)methanone,
(3-chloro-2-nitrophenyl)(4-methylphenyl)methanone,
(3-chloro-2-nitrophenyl)(4-methoxyphenyl)methanone, and
(3-chloro-2-nitrophenyl)(4-nitrophenyl)methanone,
there are obtained
2-[3-(2,4-dichlorobenzoyl)-2-nitrophenyl]propanedioic acid,
2[3-(4-methylbenzoyl)-2-nitrophenyl]propanedioic acid,
2[3-(4-methoxybenzoyl)-2-nitrophenyl]propanedioic acid, and
2-[3-(4nitrobenzoyl)-2nitrophenyl]-2-nitrophenyl propanedioic acid.

EXAMPLE 10

Following the procedure of Example 4 but substituting equal molar amounts of the following for 2-(3-benzoyl-2-nitrophenyl)propanedioic acid:
2-[3-(2,4-dichlorobenzoyl)-2-nitrophenyl]propanedioic acids,
2-[3-(4-methylbenzoyl)-2nitrophenyl]propanedioic acid,
2-[3-(4-methoxybenzoyl)-2-nitrophenyl]propanedioic acid, and
2-[3-(4-nitrobenzoyl)-2-nitrophenyl]propanedioic acid, there are obtained
3-(2,4-dichlorobenzoyl)-2-nitrobenzeneacetic acid,
3-(4-methylbenzoyl)-2nitrobenzeneacetic acid,
3-(4-methoxybenzoyl)-2-nitrobenzeneacetic acid, and
3-(4-nitrobenzoyl)-2nitrobenzeneacetic acid.

FORMULATION AND ADMINISTRATION

The present invention also contemplates novel therapeutic compositions containing the compounds of the invention as active ingredients. Effective quantities of any of the foregoing pharmacologically active compounds may be administered to a living animal body in any one of various ways; for example, orally as in capsules or tablets, parenterally in the form of sterile solutions or suspensions, and in some cases intravenously in the form of sterile solutions. In forming the novel compositions of this invention, the active ingredient is incorporated in a suitable carrier, illustratively, a pharmaceutical carrier. Suitable pharmaceutical carriers which are useful in formulating the compositions of this invention include starch, gelatin, glucose, magnesium carbonate, lactose, malt and the like. Liquid compositions are also within the purview of this invention and suitable liquid pharmaceutical carriers includes ethyl alcohol, propylene glycol, glycerine, glucose syrup and the like.

The pharmacologically active compounds may be advantageously employed in a unit dosage of from 0.1 to 250 milligrams or more depending on the size of the animal. For example, a large animal such as a horse may require tablets of 500–1000 milligrams active ingredient. The unit dosage may be given a suitable number of times daily so that the daily dosage may vary from 0.3 to 450 milligrams. Five to 25 milligrams appears optimum per unit dose.

It is only necessary that the active ingredient constitute an effective amount, i.e., such that a suitable effective dosage will be obtained with the dosage form employed. The exact individual dosages as well as daily dosages will, of course, be determined according to standard medical principles under the direction of a physician or veterinarian.

The active agents of the invention may be combined with other pharmacologically active agents, or with buffers, antacids or the like, for administration and the proportion of the active agent in the compositions may be varied widely.

The following are examples of compositions formed in accordance with this invention.

1. CAPSULES

Capsules of 5 mg., 25 mg., and 50 mg. of active ingredient per capsule are prepared. With the higher amounts of active ingredient, adjustment may be made in the amount of lactose.

| Typical blend for encapsulation | Per capsule, mg. |
|---|---|
| Active ingredient | 5.0 |
| Lactose | 296.7 |
| Starch | 129.0 |
| Magnesium stearate | 4.3 |
| | Total 435.0 mg. |

Additional capsule formulations preferably contain a higher dosage of active ingredient and are as follows.

| Ingredients | Per capsule, mg. |
|---|---|
| Active ingredient | 25.0 |
| Lactose | 306.5 |
| Starch | 99.2 |

| Ingredients | Per capsule, mg. |
|---|---|
| -continued | |
| Magnesium stearate | 4.3 |
| | Total 435.0 mg. |

In each case, uniformly blend the selected active ingredient with lactose, starch, and magnesium stearate and encapsulate the blend.

2. TABLETS

A typical formulation for a tablet containing 5.0 mg. of active ingredient per tablet follows. The formulation may be used for other strengths of active ingredient by adjustment of weight of dicalcium phosphate.

| | Per tablet, mg. |
|---|---|
| (1) Active ingredient | 5.0 |
| (2) Corn starch | 13.6 |
| (3) Corn starch (paste) | 3.4 |
| (4) Lactose | 79.2 |
| (5) Dicalcium phosphate | 68.0 |
| (6) Calcium stearate | 0.9 |
| | 170.1 mg. |

Uniformly blend 1, 2, 4, and 5. Prepare 3 as a 10 percent paste in water. Granulate the blend with starch paste and pass the wet mass through an eight mesh screen. The wet granulation is dried and sized through a twelve mesh screen. The dried granules are blended with the calcium stearate and pressed.

3. INJECTABLE—2% STERILE SOLUTIONS.

| | Per cc. |
|---|---|
| Active ingredient | 20 mg. |
| Preservative, e.g., cholorobutanol | 0.5% weight/volume |
| Water for injection | q.s. |

Prepare solution, clarify by filtration, fill into vials, seal and autoclave.

Various modifications and equivalents will be apparent to one skilled in the art and may be made in the compounds, compositions, and methods of the present invention without departing from the spirit or scope thereof, and it is therefore understood that the invention is to be limited only by the scope of the appended claims.

What is claimed is:

1. A compound selected from the group having the formula:

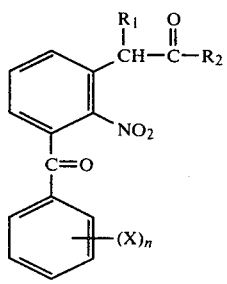

wherein;

$R_1$ is hydrogen or lower alkyl, $R_2$ is OH, OM, O-lower alkyl, $NH_2$, NH-lower alkyl or N,N-dilower alkyl, X is hydrogen, halogen, lower alkyl, lower alkoxy, trifluoromethyl or nitro, M is a pharmaceutically acceptable cation or a fraction thereof when the cation is multivalent and hydrates thereof, and n is 1-3 inclusive.

2. The compound of claim 1 which is 3-benzoyl-2-nitrobenzeneacetic acid.

3. The compound of claim 1 which is 3-(4-chlorobenzoyl)-2-nitrobenzeneacetic acid.

4. The compound of claim 1 which is 3-benzoyl-2-nitro-(α-methyl)benzeneacetic acid.

5. The compound of claim 1 which is 3-benzoyl-2-nitrophenylacetamide.

6. The compound of claim 1 which is ethyl 3-benzoyl-2-nitrophenylacetate.

7. The method of alleviating inflammation in a living animal body with a minimum of undesirable side effects comprising internally administering to said living animal body an effective amount of a compound selected from the group having the formula:

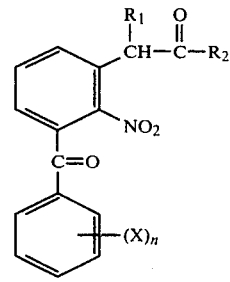

wherein;

$R_1$ is hydrogen or lower alkyl, $R_2$ is OH, OM, O-lower alkyl, $NH_2$, NH-lower alkyl or N,N-dilower alkyl, X is hydrogen, halogen, lower alkyl, lower alkoxy trifluoromethyl or nitro, M is a pharmaceutically acceptable cation or a fraction thereof when the cation is multivalent and hydrates thereof and n is 1-3 inclusive.

8. The method of claim 7 wherein the compound is 3-benzoyl-2-nitrobenzeneacetic acid.

9. The method of claim 7 wherein the compound is 3-(4-chlorobenzoyl)-2-nitrobenzeneacetic acid.

10. The method of claim 7 wherein the compound is 3-benzoyl-2-nitro-(α-methyl)benzeneacetic acid.

11. The method of claim 7 which is 3-benzoyl-2-nitrophenylacetamide.

12. The method of claim 7 wherein the compound is ethyl 3-benzoyl-2-nitrophenylacetate.

13. A therapeutic composition suitable for alleviation of inflammation with minimal side effects comprising (a) an effective amount of a compound selected from the group having the formula:

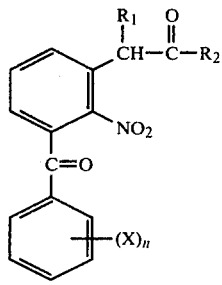

wherein:

R₁ is hydrogen or lower alkyl,

R₂ is OH, OM, O-lower-alkyl, NH₂, NH-lower alkyl or N,N-dilower alkyl,

X is hydrogen, halogen, lower alkyl, lower alkoxy, trifluoromethyl or nitro,

M is a pharmaceutically acceptable cation or a fraction thereof when the cation is multivalent and hydrates thereof and n is 1–3 inclusive, and (b) a pharmaceutically acceptable carrier therefor.

14. The therapeutic composition of claim 13 wherein the compound is 3-benzoyl-2-nitrobenzeneacetic acid.

15. The therapeutic composition of claim 13 wherein the compound is 3-(4-chlorobenzoyl)-2-nitrobenzeneacetic acid.

16. The therapeutic composition of claim 13 wherein the compound is 3-benzoyl-2-nitro-(α-methyl)benzeneacetic acid.

17. The therapeutic composition of claim 13 wherein the compound is 3-benzoyl-2-nitrophenylacetamide.

18. The therapeutic composition of claim 13 wherein the compound is ethyl 3-benzoyl-2-nitrophenylacetate.

* * * * *